United States Patent [19]
Underiner et al.

[11] Patent Number: 5,354,756
[45] Date of Patent: Oct. 11, 1994

[54] OLEFIN-SUBSTITUTED LONG CHAIN XANTHINE COMPOUNDS

[75] Inventors: Gail Underiner, Brier; David Porubek, Edmonds; J. Peter Klein, Vashon Island, all of Wash.

[73] Assignee: Cell Therapeutics, Inc., Seattle, Wash.

[21] Appl. No.: 3,372

[22] Filed: Jan. 12, 1993

[51] Int. Cl.$^5$ .................... A61K 31/52; C07D 473/02
[52] U.S. Cl. .................... 514/263; 544/267; 544/272; 544/273
[58] Field of Search .................... 544/267, 272, 273; 514/263

[56] References Cited

U.S. PATENT DOCUMENTS

| | | | |
|---|---|---|---|
| 4,755,517 | 7/1988 | Bruns et al. | 544/267 |
| 5,082,845 | 1/1992 | Wolf et al. | 544/267 |
| 5,109,003 | 4/1992 | Tanaka et al. | 544/267 |

Primary Examiner—John M. Ford
Assistant Examiner—Pavanaram K. Sripada
Attorney, Agent, or Firm—Jeffrey B. Oster; Stephen Faciszewski

[57] ABSTRACT

There is disclosed compounds and pharmaceutical compositions having a xanthine core and one or two hydrocarbon side chains bonded to a ring nitrogen atom, wherein the hydrocarbon side chains are independently a straight chain hydrocarbon having at least one double bond in a carbon chain length of from about 4 to about 18 carbon atoms in length, wherein multiple double bonds are separated from each other by at least three carbon atoms, and wherein the hydrocarbon chain may be substituted by a hydroxyl, halo or dimethylamino group and/or interrupted by an oxygen atom. The compounds lower elevated levels of unsaturated, non-arachidonate phosphatidic acid (PA) and diacylglycerol (DAG) derived from said PA within seconds of the primary stimulus and their contact with cells. The modulatory effect depends on the nature of the target cell and the stimulus applied.

12 Claims, 7 Drawing Sheets

1

OLEFIN-SUBSTITUTED LONG CHAIN XANTHINE COMPOUNDS

TECHNICAL FIELD OF THE INVENTION

The invention relates to a class of olefin-substituted long chain xanthine compounds that are effective agents to modulate cellular responses to stimuli. More specifically, the inventive compounds have at least one double bond in a long chain substituent bonded to a ring nitrogen of a xanthine core. The inventive compounds are useful antagonists to control intracellular levels of specific sn-2 unsaturated phosphatidic acids and corresponding phosphatidic acid-derived diacylglycerols which occur in response to cellular proliferative stimuli.

BACKGROUND ART

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,307 and 3,737,433. Metabolites of PTX were summarized in Davis et al., *Applied Environment Microbial.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947. In addition, U.S. Pat. Nos. 4,833,146 and 5,039,666 disclose use of tertiary alcohol analogs of xanthine for enhancing cerebral blood flow.

Furthermore, U.S. Pat. No. 4,636,507 describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. Nos. 4,965,271 and 5,096,906). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and that can maintain cellular homeostasis in the face of a variety of inflammatory stimuli. The present invention was made in a process of looking for such compounds.

SUMMARY OF THE INVENTION

We have found that the compounds described herein can be used to maintain homeostasis of a large variety of target cells in response to a variety of stimuli. In addition, the inventive compounds and compositions are suitable for normal routes of therapeutic administration and permit effective dosages to be provided.

The invention is directed to the use of olefin-substituted xanthines containing at least one and no more than six double bonds in a side chain of from about 4 to about 18 carbon atoms in length, wherein the side chain is bonded to a ring nitrogen of the xanthine core. The inventive compounds are effective in modulating cellular response to external or in situ primary stimuli, as well as to specific modes of administration of such compounds in effective amounts.

The inventive compounds comprise compounds and pharmaceutical compositions having a xanthine core of the formula:

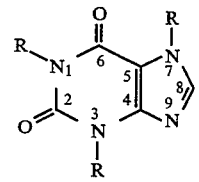

wherein each of one or two R is independently a straight chain hydrocarbon having at least one double bond in a carbon chain length of from about 4 to about 18 carbon atoms in length, wherein multiple double bonds are separated from each other by at least three carbon atoms, and wherein the hydrocarbon chain may be substituted by a hydroxyl, halo or dimethylamino group and/or interrupted by an oxygen atom. Preferably, each double bond (with the exception of a terminal olefin) is in a cis configuration. Preferably, the hydrocarbon side chain is bonded to a ring nitrogen of xanthine directly, or through an amino or ether linkage. Preferably, the length of the hydrocarbon chain is from six to twelve carbon atoms in length and contains one or two double bonds.

The present invention further provides a pharmaceutical composition comprising an inventive compound and a pharmaceutically acceptable excipient, wherein the pharmaceutical composition is formulated for oral, parenteral or topical administration to a patient.

The present invention further provides a method for treating an individual having a variety of diseases, wherein the disease is characterized by or can be treated by inhibiting an immune response or a cellular response to external or in situ primary stimuli, wherein the cellular response is mediated through a specific phospholipid-based second messenger acting adjacent to the inner leaflet of the cell membrane of a cell. The second messenger pathway is activated in response to various noxious or proliferative stimuli characteristic of a variety of disease states and the biochemistry of this second messenger pathway is described herein. More specifically, the invention is directed to methods to treat or prevent clinical symptoms of various disease states or reduce toxicity's of other treatments by inhibiting cellular signaling through the second messenger pathway described herein. The disease states or treatment-induced toxicity's are selected from the group consisting of proliferation of tumor cells in response to an activated oncogene; hematocytopenia caused by cytoreductive therapies; autoimmune diseases caused by a T cell response or a B cell response and antibody production; septic shock; resistance of mesenchymal cells to tumor necrosis factor (TNF); proliferation of smooth muscle cells endothelial cells, fibroblasts and other cell types in response to growth factors, such as PDGF-AA, BB, FGF, EGF, etc.(i.e., atherosclerosis, restenosis, stroke, and coronary artery disease); human immunodeficiency virus infection (AIDS and AIDS related complex); proliferation of kidney mesangial cells in response to IL-1 mip-1α, PDGF or FGF; inflammation; kidney glomerular or tubular toxicity in response to cyclosporin A or amphotericin B treatment; organ toxicity (e.g., gastrointestinal or pulmonary epithelial) in response to a cytoreductive therapy (e.g., cytotoxic drug or radiation); enhancing antitumor effects of nonalkylating antitumor agents; allergies in response to inflammatory stimuli (e.g., TNF, IL-1 and the like) characterized by production of cell surface metalloproteases or by degranulation of mast cells and basophils in response to IgE, bone diseases caused by overproduction of osteoclast-activating factor (OAF) by osteoclasts, CNS diseases caused by reduced signal transduction of the neurotransmitters epinephrine and acetylcholine, and combinations thereof.

BRIEF DESCRIPTION OF THE DRAWINGS

FIG. 5 shows an analysis of mean fluorescence intensity of cells analyzed by flow cytometry.

FIG. 6 shows that CT1508 strongly inhibited gene expression (i.e., possessed strong antitumor activity) when compared with an alcohol derivative (CT1501R).

DETAILED DESCRIPTION OF THE INVENTION

Figure 1:
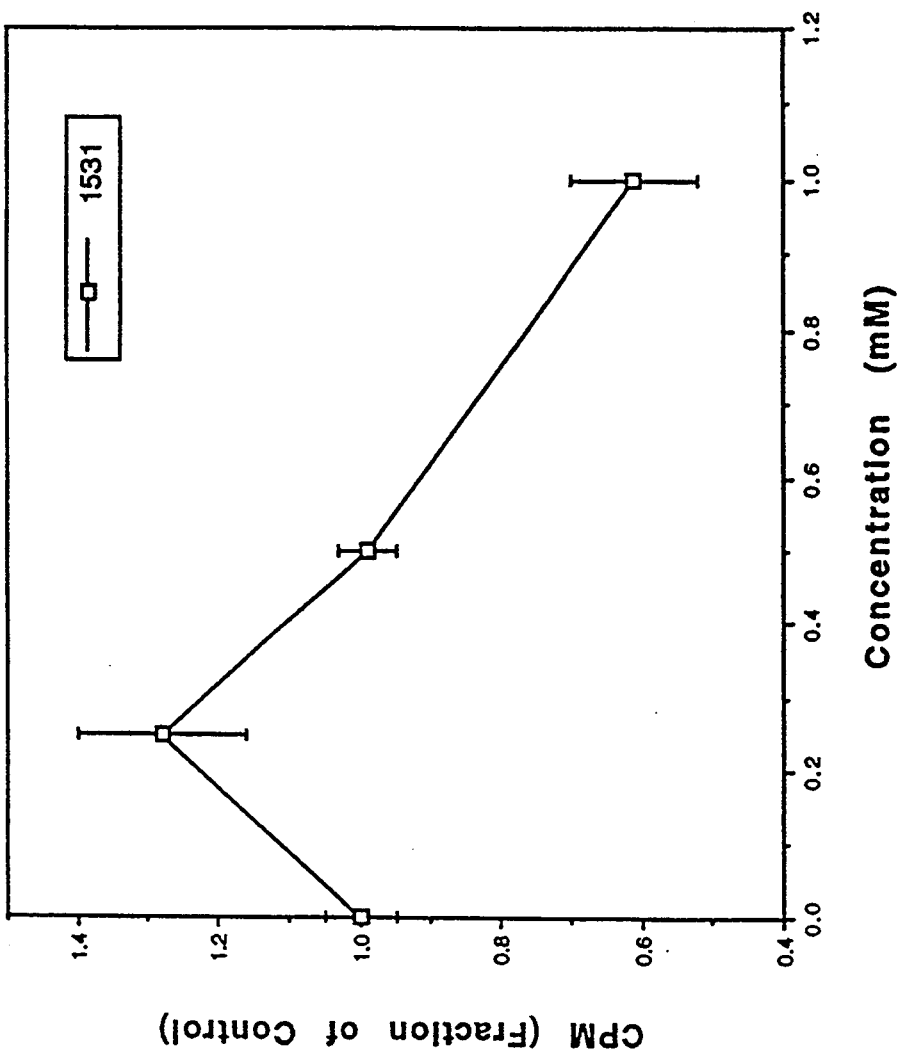
FIG. 1 shows a mixed lymphocyte reaction of inventive compound CT1531 (N-(2-propenyl)theobromine). The mixed lymphocyte reaction shows a proliferative response of PBMC (peripheral blood mononuclear cells) to allogeneic stimulation determined in a two-way mixed lymphocyte reaction. CT1531 showed dose-response activity in this immune modulating activity assay procedure.

The invention is directed to a defined genus of inventive compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A-2.
PLD=phospholipase D
PAA=phosphoarachidonic acid
PLA-2=phospholipase A2
PC=phosphatidyl choline
"remodeled" PA, cyclic pathway=PAA, LPA, PA and DAG intermediates substituted with L-saturated, 2-linoleoyl or 1,2-dileolyl/1,2-sn-dilinoleoyl at the indicated sn-1 and sn-2 positions.
"Classical PI Pathway"=PI, DAG, PA intermediates substituted with 1-stearoyl, 2-arachidonoyl fatty acyl side chains.
"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaneoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as interleukin-1 or TNF) acting at a receptor on a cellular surface. An immediate detectable effect is an elevation of levels of PA and DAG. Administration of the compounds of the invention reverse this elevation.

The compounds of the invention, include inhibitors of subspecies of LPAAT in PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl,2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

In Vitro Assays for Physiologic and Pharmacologic Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at $1000 \times g$ for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 $\mu$l complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 $\mu$Ci/well of 40 to 60 Ci/mmole) and proliferation determined by liquid scintillation counting.

A thymocyte costimulator assay is conducted to evaluate the inventive compounds to inhibit activation and proliferation of thymocytes caused by stimulation with Con A and interleukin-1 (IL-1), or interleukin-1 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2 \times 10^5$ cells/well) and a stimulating agent, such as Con A, IL-1 (e.g., IL-1$\alpha$) or IL-2 is added to the well. The cells are incubated for 4 days at 37° C. On the fourth day, the cells are pulsed with tritiated thymidine and cell proliferation determined. Inventive compounds are added at the time of stimulating agent addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microliter plates and drug is added about two days after plating. Cell viability is determined using a fluorescent viability stain (e.g., 2′,7′-bis-(2-carboroxyethyl)-5-(and-6)- carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1$\alpha$ or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 $\mu$g/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Drug inhibitory activity can also be measured by determining levels of vascular cell adhesion molecule (VCAM) in stimulated cells. Early passage human umbilical vein endothelial cells (HUVEC) (obtained from commercial suppliers such as Cell Systems, Inc. or Clonetics) are cultured in media (e.g., Hepes buffered media, Cell Systems) containing 10% fetal bovine serum, and supplemented with a stimulating agent, such as fibroblast growth factor (acidic FGF, Cell Systems, Inc.) or TNF. The cells are plated into wells of a microliter plate (e.g., $5 \times 10^4$ per well) and allowed to incubate at 37° C. for 72 hrs. The resting cells are removed (e.g., 20–30 min treatment with 0.4% EDTA), washed in media (e.g., phosphate buffered saline plus 0.1% bovine serum albumin with 0.01% sodium azide) and labeled on ice with a monoclonal antibody ("first antibody") recognizing human VCAM (e.g., 1 $\mu$g of a murine monoclonal antibody recognizing human VCAM Genzyme). After 60 min on ice, the cells are washed (preferably twice) with cold wash media and incubated with an antibody that recognizes the first antibody, (e.g., 1 $\mu$g of goat anti-mouse IgG conjugated with phycoerythrin, CalTag, Inc.). After 30 min on ice, the cells are washed twice and analyzed on a flow cytometer (Coulter Elite ®) at appropriate emission and excitation wavelengths (e.g., for phycoerythrin use excitation at 488 nm and emission at 525 nm).

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine bmin; plasma membrane-enriched microsomes, plasma membranes derived as described in Bursten et al. (*J. Biol. Chem.* 226:20732-20743, 1991), or detergent-solubilized microsomes; synaptosomes, and membranes or other cell preparations solubilized using, for example, NP-40, Miranal, SDS or other neutral detergents; and detergent-solubilized or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, *Biochemistry* 30:6195-6203, 1991. A Rainin ® mu-Porasil column is used with a 3:4 hexane:propanol organic carrier and a 1-10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5-60 seconds after stimulation with the primary stimulus, such as a cytokine. This technique permits assessment of the levels of various lipid components as a function of time.

An inventive compound can be assayed for activity protecting TNF-mediated cytotoxicity. In this assay, L929 murine fibroblast cells ($10^4$ cells per well) are incubated with either compounds at varying doses and media control for two hrs. TNF-α (R&D Systems) is added at a concentration of 500 pg/ml, which is four times the LD50 of TNF (125 pg/ml). The cells plus (or minus) drug plus TNF were incubated for 40 hrs at 37° C. The media is removed and replaced with fresh media containing 2% serum and 10 μg/ml of BCECF fluorescent dye and incubated for 30 min. The fluorescent dye-containing media is removed and replaced with PBS (phosphate buffered saline) and each well was assayed for fluorescence.

Another assay measures the effects of drug to inhibit adhesion of U937 cells to TNF-activated HUVEC cells In this experiment, HUVEC cells are induced with human TNF-α (20 ng/ml) and drug at varying concentrations for 14-16 hrs. U937 cells (a human monocyte cell line) are incubated and labeled with BCECF (10 μg/ml), a fluorescent dye. The U937 cell preparation (2.5 $\times 10^4$ cells per well) is layered on top of the activated HUVEC cells. The cells are reverse spun to remove partially adhering and nonadhering U937 cell. The adherent U937 cells are measured by fluorescence on a fluorescent plate reader.

Compounds of the Invention

The invention is directed to the use of olefin-substituted xanthines containing at least one and no more than six double bonds in a side chain of from about 4 to about 18 carbon atoms in length, wherein the side chain is bonded to a ring nitrogen of the xanthine core. The inventive compounds are effective in modulating cellular response to external or in situ primary stimuli, as well as to specific modes of administration of such compounds in effective amounts.

The inventive compounds comprise compounds and pharmaceutical compositions having a xanthine core, wherein each of one or two hydrocarbon side chains bonded to a ring nitrogen atom are independently a straight chain hydrocarbon chain having at least one double bond in a carbon chain length of from about 4 to about 18 carbon atoms in length, wherein multiple double bonds are separated from each other by at least three carbon atoms, and wherein the hydrocarbon chain may be substituted by a hydroxyl, halo or dimethylamino group and/or interrupted by an oxygen atom. Preferably, each double bond (with the exception of a terminal olefin) is in a cis configuration. Preferably, the hydrocarbon side chain is bonded to a ring nitrogen of xanthine directly, or through an amino or ether linkage. Preferably, the length of the hydrocarbon chain is from six to twelve carbon atoms in length and contains one or two double bonds.

Those embodiments are preferred wherein a single hydrocarbon chain (e.g., R) is at position 1 of this xanthine nucleus, or where the hydrocarbon chains are at position 1 and 7. Also preferred, are those compounds of the invention wherein a single R substituent is at position 7 of the xanthine nucleus.

The present invention further comprises a pharmaceutical composition comprising one or a plurality of inventive compounds and a pharmaceutically acceptable carrier or excipient. The individuals to be treated with an inventive compound or inventive pharmaceutical composition may either be contacted with the compound of the invention in vitro culture, in an extracorporeal treatment, or by administering (oral, parenteral or topical) the compound of the invention or pharmaceutical composition to a subject whose cells are to be treated.

Illustrative compounds of the invention include both cis and trans olefins of the following compounds:

| CT1508 | N-(6-cis-nonenyl) theobromine |
| CT1531 | N-(2-propenyl) theobromine |
| CT1534 | N-(6-heptenyl) theobromine |
| CT1535 | N-(7-octenyl) theobromine |
| CT1539 | N-(5-hexenyl) theobromine |
| CT1550 | N-(8-nonenyl) theobromine |

| | |
|---|---|
| -continued | |
| CT1563 | N-(9,10-decenyl) theobromine |

Uses of the Invention Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells whose behavior is to be modified with an effective amount of an inventive compound or a pharmaceutical composition thereof wherein said method is: (1) a method to inhibit proliferation of tumor cells and said amount is sufficient to inhibit said proliferation; or (2) a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said mount is sufficient to suppress said activation; or (5) a method to enhance the resistance of mesenchymal cells to the cytotoxic effect of tumor necrosis factor and said amount is sufficient to enhance said resistance; or (6) a method to suppress antibody production of B-cells in response to an antigen, IL-4 or CD40 ligand and said amount is sufficient to suppress said antibody production; or (7) a method to inhibit the proliferation of smooth muscle cells in response to growth factors capable of stimulating said proliferation and said mount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or mip-1α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of mip-1α by IL-1, TNF, or endotoxin stimulated monocytes and macrophages; or (16) a method to prevent the release of platelet activating factor by IL-1, TNF, or endotoxin treated megakaryocytes, fibroblastic cells, and macrophages; or (17) a method to prevent the down-regulation of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitters dopamine, epinephrine, or norepinephrine, or the neurotransmitter acetylcholine, and said amount is sufficient to modulate such slow currents.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients'-cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7-10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Compounds of Formula 1 are able to increase the percentage of patients who survive. The percentage of fatalities within the first 100 days that is considered acceptable is 15-20% for "good risk" patients and 30-40% for "high risk". These fatalities are due to the direct effects of high doses of chemo/radiation. In addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, sinus dminage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV1, changes in vital capacity, and extensive mucus production.

Other suitable subjects for the administration of compounds of the invention, include patients being administered cytoreductive agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiting such treatment as an effective oral, parenteral, or intravenous sublethal dose of about 200 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Coadministration With a P-450 Inhibitor

The coadministration in vivo of the compounds of the invention along with an inhibitor of P-450 results in an enhanced effect due to a longer half life of the inventive compounds. This in vivo effect is due to inhibition of a degradation pathway for the compounds of the invention; in particular, dealkylation at the N7 position of the xanthine ring. For example, NIH3T3-D5C3 cells can be used to compare effects of an inventive compound alone or in combination with a P-450 inhibitor by comparing transformation phenotype control, incubation with an inventive compound alone, and coincubation of an inventive compound with the P-450 enzyme inhibitor.

Compounds that inhibit P-450 include, for example, (mg range daily dosage) propranolol (20–100), metaprolol (20–100); verapamil (100–400), diltiazem (100–400), nifedipine (60–100); cimetidine (400–2,400); ciprofloxacin (500–2000), enoxacin (500–2,000), norfloxacin (500–2000), ofloxacin (500–2,000), pefloxacin (500–2,000); erythromycin (100–1,000), troleandomycin (100–1,000); ketoconizole (100–2,000), thiabenzadole (100–1,000); isoniazid (100–1000); mexiletine (100–1,000); and dexamethasone (1–100 mg).

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

Depending on the inventive compound selected, the level of dosage can be appreciably diminished by coadministration of a P-450 inhibitor, such as the quinolone. Alternatively, a strong synergistic effect may be obtained with such a quinolone.

The invention is illustrated by the following examples which should not be regarded as limiting the invention in any way. In these examples PTX means pentoxifylline.

EXAMPLE 1

This example illustrates a method for synthesis of CT1508 1-(6-cis-Nonenyl)-3,7-dimethylxanthine. cis-6-Nonen-1-ol (3.00 g, 21.1 mmol) and methanesulfonyl chloride (1.6 ml, 2.4 g, 21 mmol) in $CH_2Cl_2$ (100 ml) at 0° C. was treated with triethylamine (4.4 ml, 3.2 g, 32 mmol). After 1 h the ice bath was allowed to melt. After reaching room temperature, the reaction was poured into a separatory funnel containing water (50 ml) and $CH_2Cl_2$ (50 ml). The layers were separated and the aqueous layer washed with $CH_2Cl_2$ (2×50 ml). The organic layers were combined, dried ($Na_2SO_4$), and solvent removed to give 6-cis-nonene-1-methanesulfonate as a yellow oil (4.14 g, 18.8 mmol, 89% yield), which was used without further purification.

Theobromine (3.36 g, 18.8 mmol) and sodium hydride (451 mg, 18.8 mmol) in dimethyl sulfoxide (DMSO, 40 ml) was stirred for 40 min, after which the mesylate (4.14 g, 18.8 mmol) was added. The reaction mixture was stirred at 25° C. for 3 days, heated at 80° C. for 1 hr, then cooled. The reaction mixture was poured into water (100 ml) and extracted with $CH_2Cl_2$ (3×60 ml). The organic layers were combined and washed with brine (2×50 ml) and dried ($Na_2SO_4$). The solvent was removed and the residue chromatographed (silica/ethyl acetate) to give CT1508 as a white solid (4.54 g, 79% yield).

EXAMPLE 2

This example illustrates a synthesis procedure for N-(7-octenyl)-3,7-dimethylxanthine (CT1535). DMSO (10 ml) and theobromine (540 mg, 3.0 mmol) were placed into a dry glass reaction vessel and stirred with a stir bar at room temperature. Sodium hydride (72 mg, 3.0 mmol) was added and stirred continued until evolution of hydrogen gas was essentially complete. 8-Bromo-1-octene (600 mg, 3.1 mmol) was added and the mixture was stirred for three days. The reaction was stopped by addition of 0.1N HCl (200 ml), and the mixture was extracted with dichloromethane (2×100 ml) and the organic portions pooled and dried over anhydrous magnesium sulfate. The salts were removed by filtration and the solvent was removed by rotary evaporation to leave a white solid, which was CT1535.

EXAMPLE 3

This example illustrates a synthesis procedure for N-(2-propenyl)-3,7-dimethylxanthine (CT1531). DMSO (10 ml) and theobromine (540 mg, 3.0 mmol) were placed into a dry glass reaction vessel and stirred with a stir bar at room temperature. Sodium hydride (72 mg, 3.0 mmol) was added and stirred continued until evolution of hydrogen gas was essentially complete. Allyl bromide (400 mg, 3.3 mmol) was added and the mixture was stirred for 15 hrs. The reaction was stopped by addition of 0.1N HCl (200 ml), and the mixture was extracted with dichloromethane (2×100 ml) and the organic portions pooled and dried over anhydrous magnesium sulfate. The salts were removed by filtration and the solvent was removed by rotary evaporation to leave a white solid, which was CT1531 that was recrystalized from hexane/isopropanol (1:1 ).

EXAMPLE 4

This example illustrates a synthesis procedure for N-(8'-nonenyl)-3,7dimethylxanthine (CT1550). Mesyl chloride (120 g, 813 µl, 10.5 mmol) followed by triethylamine (1.59 g, 15.8 mmol) was added to a solution of 8-nonene-1-ol (1.5 g, 10.5 mmol) in dichloromethane 100 ml) at 0° C. The reaction mixture was stirred for one hr at 0° C. and then allowed to warm to room temperature. The warmed reaction mixture was poured into 100 ml water and extracted with dichloromethane (3×50 ml). The organic portions were combined, dried with sodium sulfate and evaporated to provide a yellow oil of 8-nonene-1-mesylate (2.25 g, 97% yield).

A suspension of NaH (600 mg of a 50% mineral oil slurry, 12 mmol) in DMSO (15 ml) was added to theobromine (1.98 g, 11 mmol), and after 15 min, the 8-nonene-1-mesylate (2.25 g, 11 mmol) was added and the reaction mixture stirred for six days at 25° C. The mixture was poured into water (60 ml) and extracted with dichloromethane (3×50 ml). The organic portions were combined, dried with sodium sulfate, and evaporated to give a dark oil. The oil was chromatographed (silica, ethyl acetate) to give CT1550 as a colorless oil (810 mg, 26% yield).

EXAMPLE 5

This example illustrates method for synthesizing CT1563 (N-(9'-decenyl)-3,7-dimethylxanthine). Mesyl chloride (220 g, 1.5 ml, 19.2 mmol) followed by triethylamine (2.91 g, 28.8 mmol) was added to a solution of 9-decene-1-ol (3.00 g, 19.2 mmol) in dichloromethane (100 ml) at 0° C. The reaction mixture was stirred for 15 min at 0° C. and then allowed to warm to room temperature. After two hours, the warmed reaction mixture was poured into 100 ml water and extracted with dichloromethane (3×60 ml). The organic portions were combined, dried with sodium sulfate and evaporated to provide a yellow oil of 9-decene-1-mesylate (4.52 g, 100% yield).

A suspension of NaH (461 mg of a 50% mineral oil slurry, 19.2 mmol) in DMSO (30 ml) was added to theobromine (3.45 g, 19.2 mmol), and after 15 min, the 9-decene-1-mesylate (2.25 g, 11 mmol) was added and the reaction mixture stirred for 18 hrs at 25° C., then at 100° C. for 40 min. The mixture was poured into water (100 ml) and extracted with dichloromethane (3×50 ml). The organic portions were combined, washed with brine (60 ml), dried with magnesium sulfate, and evaporated to give a white solid. The solid was recrystalized to give CT1563 as a colorless oil (3.40 g, 56% yield).

EXAMPLE 6

This example illustrates a synthesis for CT1539 (N-(5-hexenyl)-3,7-dimethylxanthine. To a mixture of theobromine (5.53 g, 30.66 mmol) in 50 ml DMSO was added sodium hydride (883 mg, 36.79 mmole) with vigorous stirring for 10 min after which a viscous slurry formed. To the mixture was added dropwise 6-bromo-1-hexene (5 g, 30.66 mmol) in 20 ml of DMSO. After stirring for 23 hr, the mixture was treated with water (100 ml) and extracted with ether (3×100 ml). The combined extracts were washed with water (2×50 ml), dried with magnesium sulfate and the solvent evaporated under vacuum to yield white crystals (7.7 g, 29.39 mmol, 95.5% yield) of CT1539.

EXAMPLE 7

This example illustrates the effect of CT1531 as an immune modulator. FIG. 1 shows a mixed lymphocyte reaction of CT1531 (N-(2-propenyl)theobromine). The mixed lymphocyte reaction shows a proliferative response of PBMC (peripheral blood mononuclear cells) to allogeneic stimulation determined in a two-way mixed lymphocyte reaction. CT1531 was effective in this immune modulating activity assay procedure.

EXAMPLE 8

Figure 2:
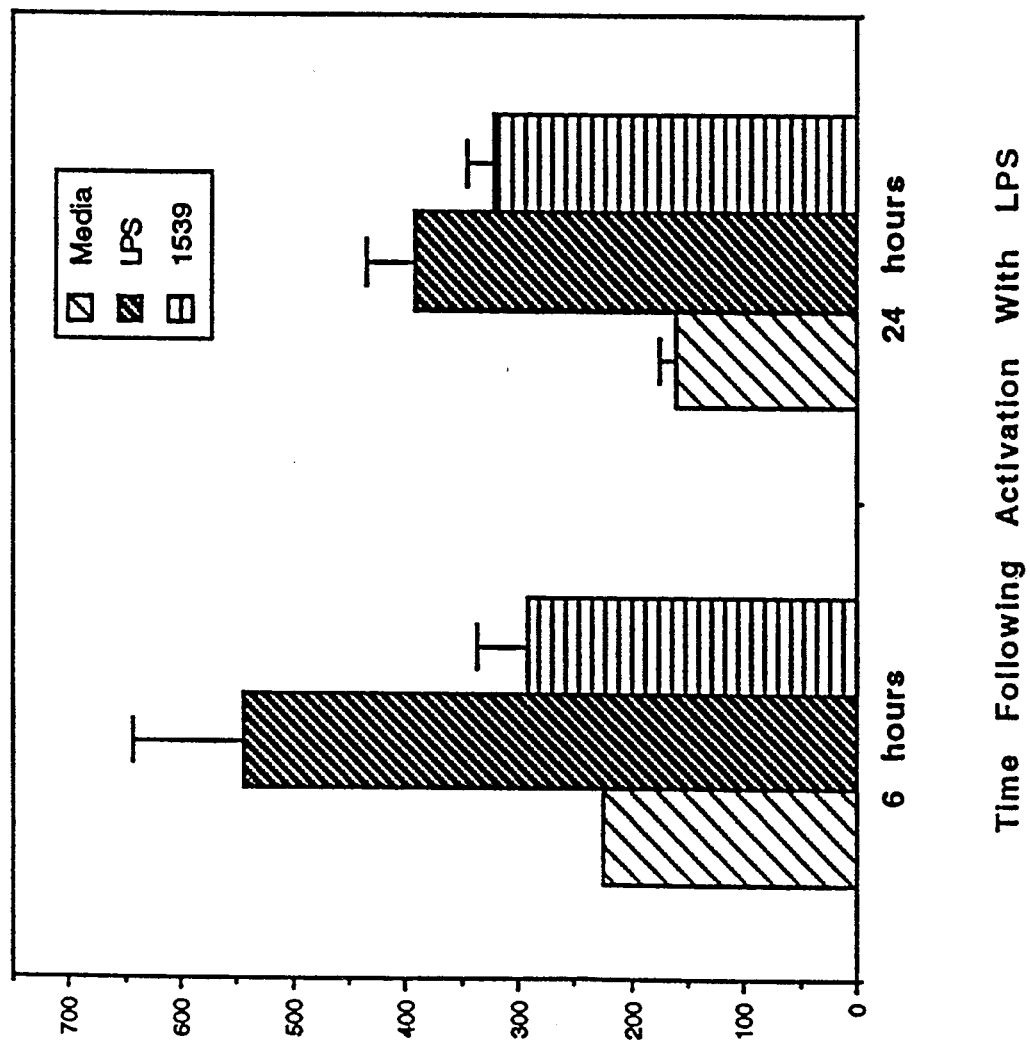
FIG. 2 shows the effects of CT1539 (N-(5-hexenyl) theobromine) on interleukin-1 alpha (IL-1α)release from P388D1 cells by the endotoxin LPS (lymphopolysaccharide). The P388D1 cells were treated with LPS at 10 μg/ml in media and the supernatants were assayed for TNFα levels (tumor necrosis alpha) levels at 6 or 24 hours following LPS administration. CT1539 was administered at a dose of 0.25 mM one hour prior to LPS treatment. The data provided in FIG. 2 show that CT1539 retarded TNF release. These data show that CT1539 has activity for treating endotoxin-induced septic shock.

This example illustrates the effects of CT1539 (N-(5-hexenyl)theobromine) on interleukin-1 alpha (IL-1α) release from P388D1 cells by the endotoxin LPS (lymphopolysaccharide). The P388D1 cells ($10^5$) were treated with LPS at 10 µg/ml in RPMI media containing 10% fetal calf serum and the supernatants were assayed for TNFα levels (tumor necrosis alpha) by an ELISA procedure at 6 or 24 hours following LPS administration. CT1539 was administered at a dose of 0.25 mM one hour prior to LPS treatment. The data provided in FIG. 2 show that CT1539 retarded TNF release. These data show that CT1539 has activity for treating endotoxin-induced septic shock.

EXAMPLE 9

Figure 3:
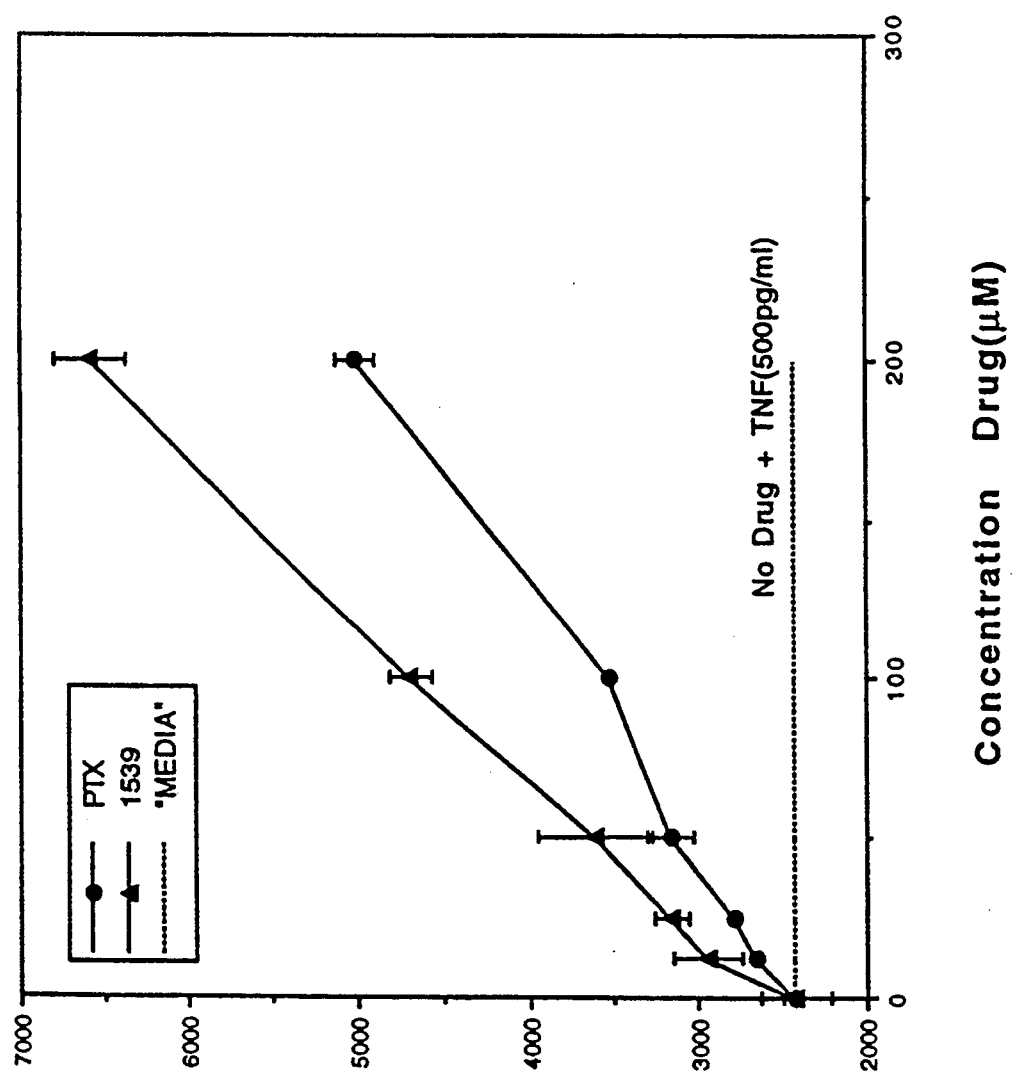
FIG. 3 shows CT1539 and PTX effects to protect murine L929 cells from the cytotoxic effects of TNF. The L929 cells were treated with 300 pg/ml of human TNF with or without drug (CT1539 or PTX). The drag was added one hour prior to TNF addition. One day later, the cells were stained for viability and counted by a fluorescense technique. The data presented in FIG. 3 show dose response activity of CT1539 and PTX in protecting cells from TNF toxicity.

This example illustrates the effects of CT1539 and PTX effects to protect murine L929 cells from the cytotoxic effects of TNF. The L929 cells ($10^5$ cells/well) were treated with 300 pg/ml of human TNF with or without drug (CT1539 or PTX). The drug was added one hour prior to TNF addition. One day later, the cells were stained for viability (using the dye BCECF) and counted by a fluorescense technique using a Milipore fluorescence plate reader. The data presented in FIG. 3 show dose response activity of CT1539 and PTX in protecting cells from TNF toxicity.

EXAMPLE 10

Figure 4:
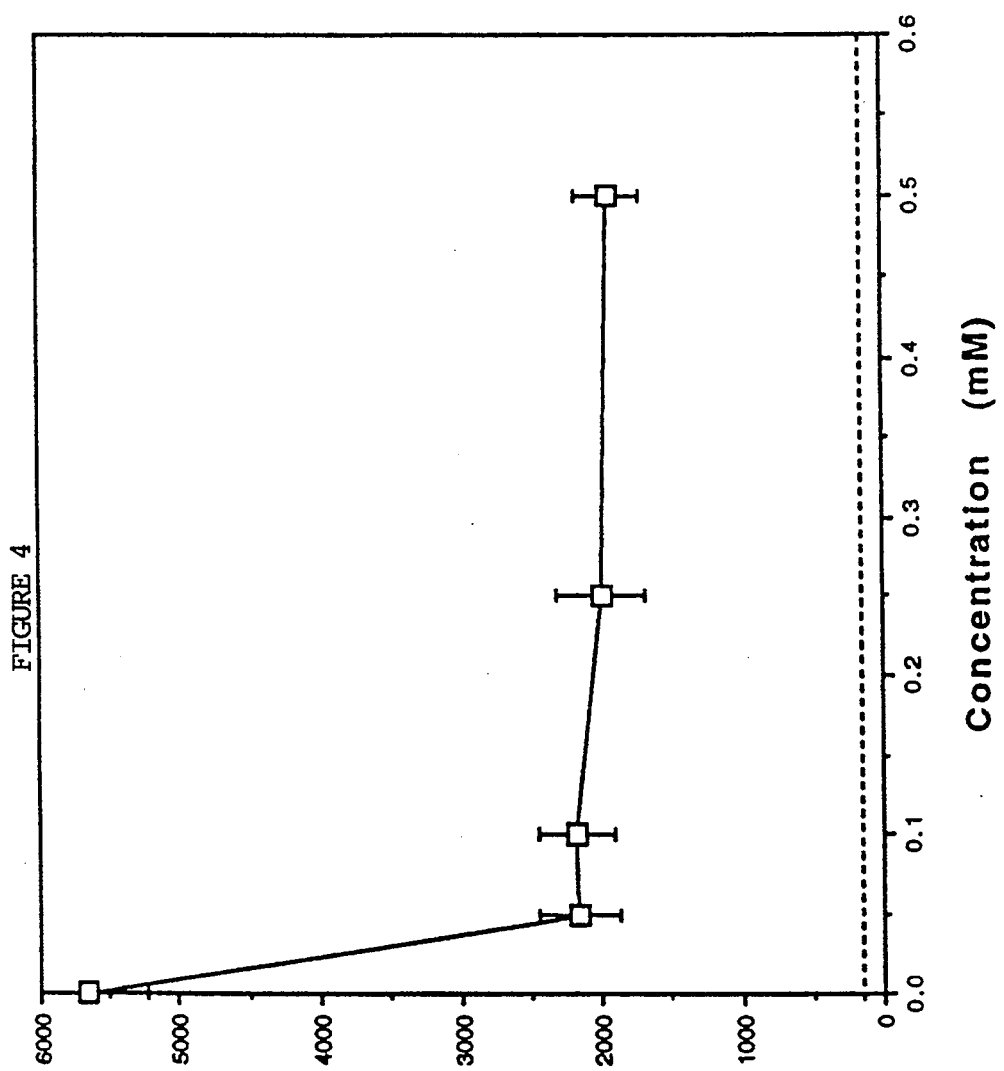
FIG. 4 shows the effect of CT1539 to inhibit adhesion of U937 cells to activated human umbilical vein endothelial cells (HUVEC). HUVEC cells were activated with 20 ng/ml of human TNF for 12 hours. CT1539 was added to the samples one hour prior to adding TNF. U937 cells were preloaded with a fluorescent dye were added to the HUVEC cells and adhesion measured after washing. CT1539 reduced adhesion, but not in a dose-dependent manner.

This example illustrates the effect of CT1539 to inhibit adhesion of U937 cells to activated human umbilical vein endothelial cells (HUVEC). HUVEC cells (4000/well, seeded 72 hrs in advance) were activated with 20 ng/ml of human TNF for 12 hours. CT1539 was added to the samples one hour prior to adding TNF. U937 cells were preloaded with a fluorescent dye (BCECF) were added to the HUVEC cells for 30 min and washed twice with PBS (phosphate buffered saline) and adhesion measured by fluorescence on a fluorescence plate reader. As shown in FIG. 4, CT1539 reduced adhesion, but not in a dose-dependent manner. Background adhesion is shown as a dashed line.

EXAMPLE 11

Figure 5:
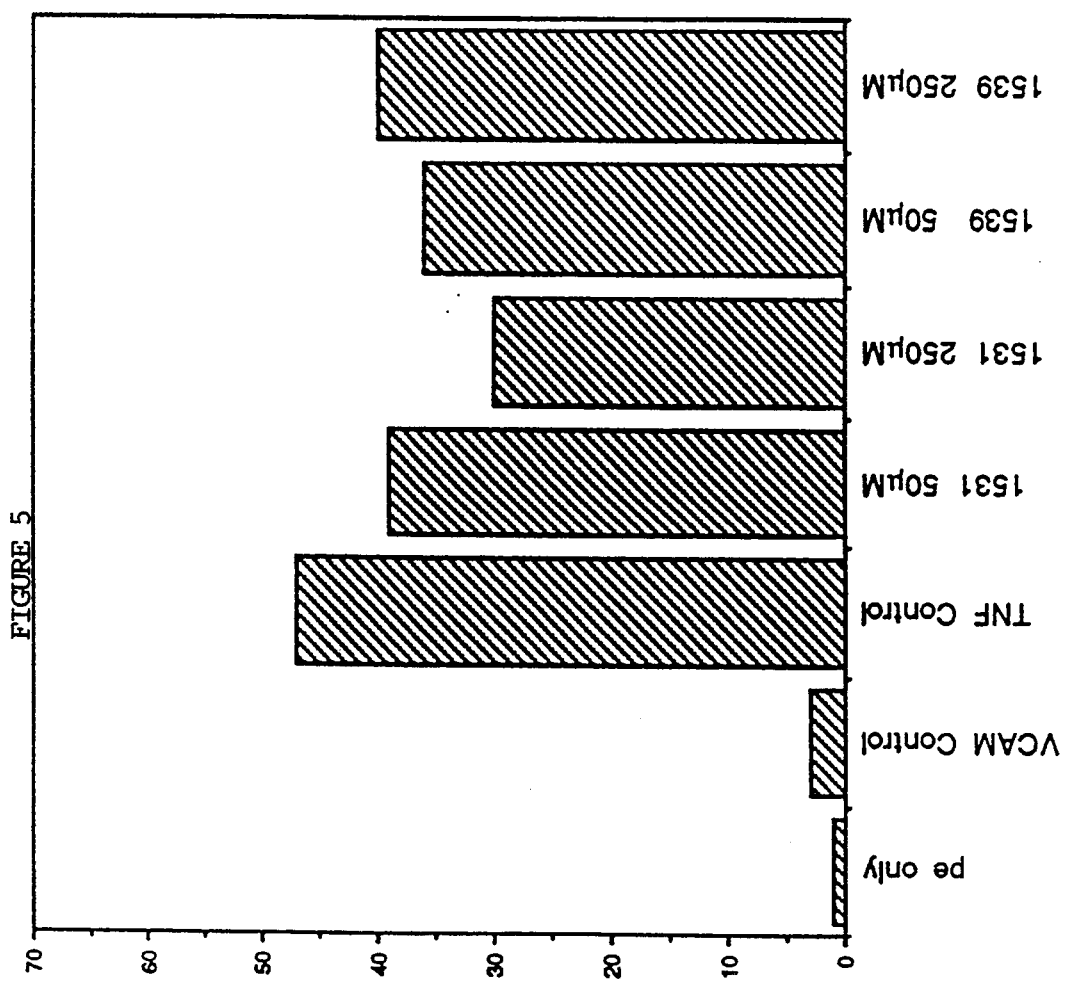
FIG. 5 shows the effects of CT1531 and CT1539 to inhibit cell surface expression of VCAM in HUVEC cells. The cells were stimulated with TNF-α (20 ng/ml) for 20 hrs and then stained for immunofluorescence using a monoclonal antibody recognizing VCAM, followed by a goat anti-mouse antibody conjugated to phycoerythrin. The cells were analyzed for antibody binding using flow cytometry.

This example illustrates the effects of CT1531 and CT1539 to inhibit cell surface expression of VCAM in HUVEC cells. The cells were stimulated with TNF-α (20 ng/ml) for 20 hrs and then stained for immunofluorescence using a monoclonal antibody recognizing VCAM, followed by a goat anti-mouse antibody conjugated to phycoerythrin. The cells were analyzed for antibody binding using flow cytometry. FIG. 5 shows an analysis of mean fluorescence intensity of 10,000 cells analyzed by flow cytometry.

EXAMPLE 12

Figure 6:
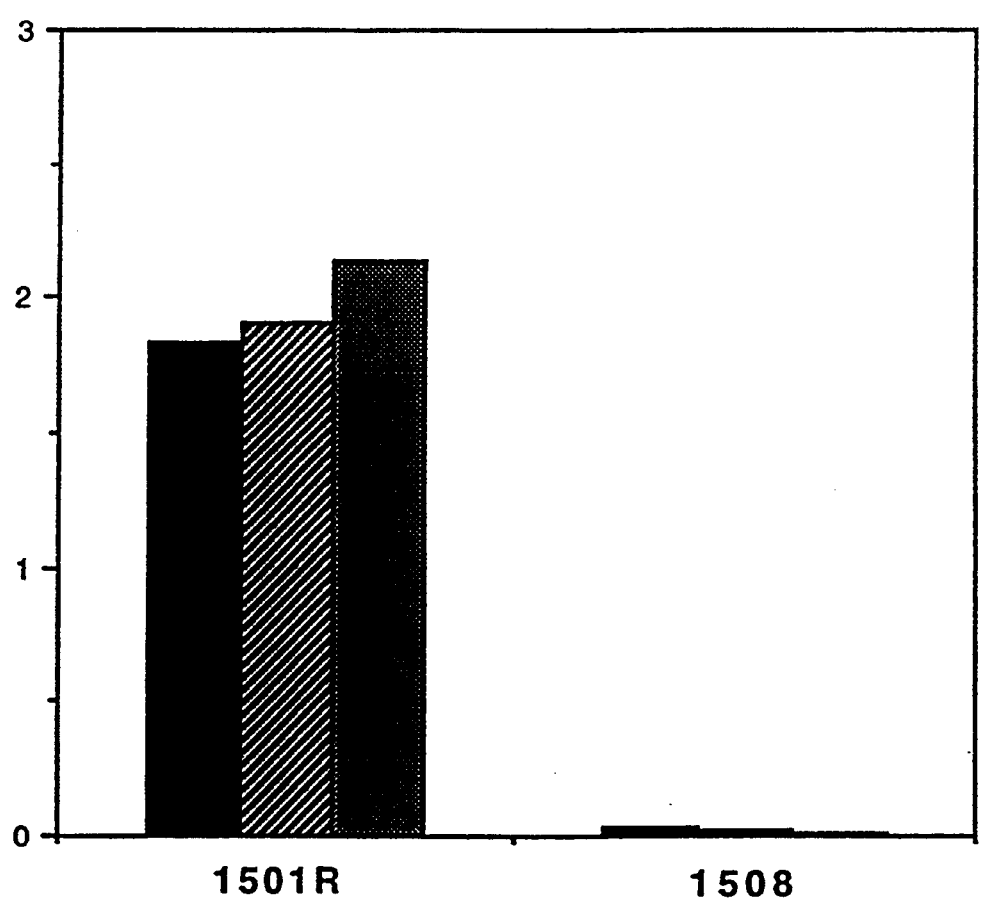
FIG. 6 illustrates the effects of CT1508 (N-(6-cis-nonenyl) theobromine on cell proliferation as a measure of antitumor activity and the ability of CT1508 to inhibit gene expression in tumor cells. A specific plasmid construct employing a human CMV (cytomegalovirus) promoter directs the expression of a reporter gene (secreted human placental alkaline phosphatase) that was transformed into the tumor cell line 293-EBNA cells. The cells were treated with various concentrations of drug. Antitumor activity was measured in culture supernatants by expression of alkaline phasphatase reporter gene by absorbance at 405 nm of cell conditioned medium in the presence of substrate (e.g., ortho-nitrophenol phosphate) as described in Berger et al. (*Gene* 66: 1–10, 1988).

This example illustrates the effects of CT1508 (N-(6-cis-nonenyl) theobromine on cell proliferation as a measure of antitumor activity and the ability of CT1508 to inhibit gene expression in tumor cells. A specific plasmid construct employing a human CMV (cytomegalovirus) promoter directs the expression of a reporter gene (secreted human placental alkaline phosphatase) that was transformed into the tumor cell line 293-EBNA cells. The cells were treated with various concentrations of drug. Antitumor activity was measured in culture supernatants by expression of alkaline phasphatase reporter gene by absorbance at 405 nm of cell conditioned medium in the presence of substrate (e.g., ortho-nitrophenol phosphate) as described in Berger et al. (*Gene* 66:1–10, 1988). FIG. 6 shows that CT1508 strongly inhibited gene expression (i.e., possessed strong antitumor activity) when compared with an alcohol derivative (CT1501R).

EXAMPLE 13

Figure 7:
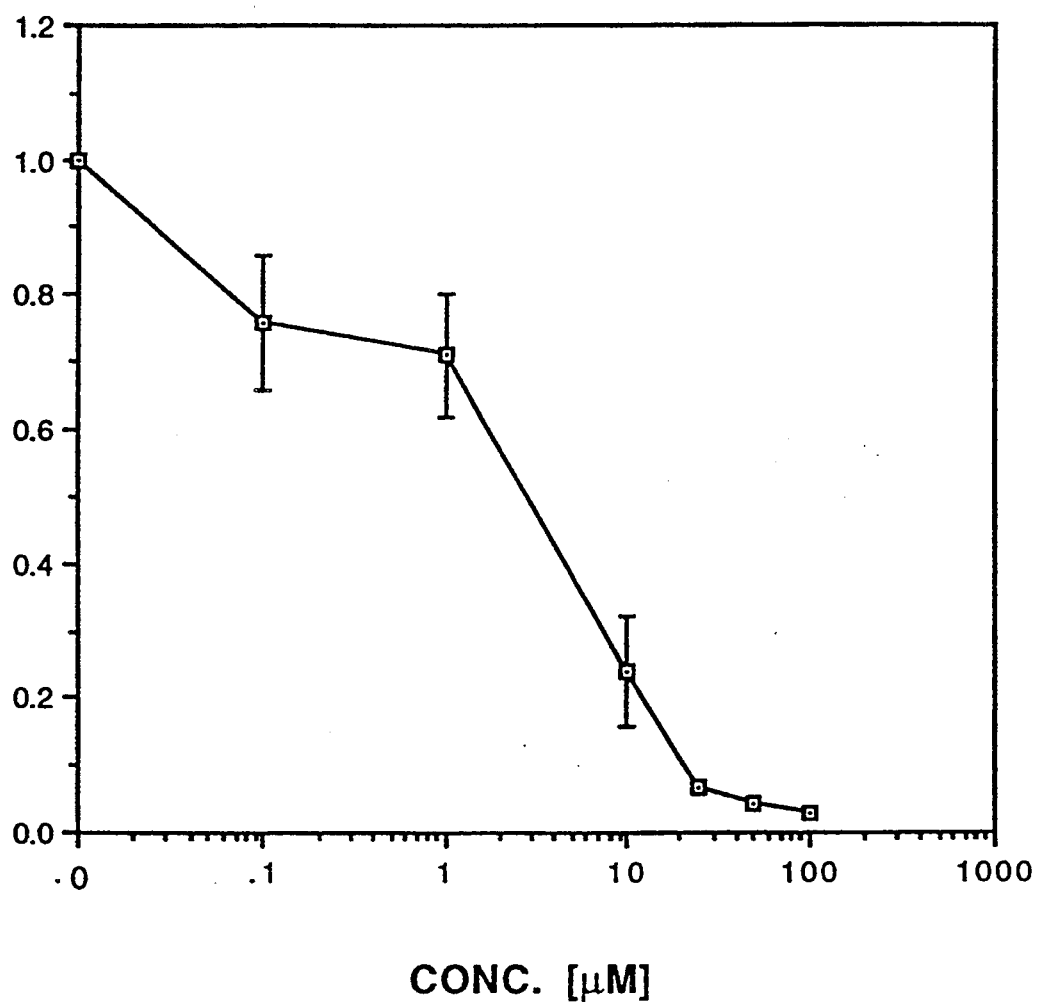
FIG. 7 illustrates the ability of CT1508 to strongly inhibit proliferation of human stromal cells when stimulated with PDGF. This assay is a model for restenosis and treatment of atherosclerosis and coronary artery disease. As can be seen from FIG. 7, the IC50 of CT1508 to inhibit stromal cell proliferation stimulated by PDGF BB and IL-1α was about 3 μM. This concentration is readily achievable in vivo in patients with administration of about 300 to 500 mg two or three times daily to a 70 kg person.

This example illustrates the ability of CT1508 to strongly inhibit proliferation of human stromal cells when stimulated with PDGF. This assay is a model for restenosis and treatment of atherosclerosis and coronary artery disease. As can be seen from FIG. 7, the IC50 of CT1508 to inhibit stromal cell proliferation stimulated by PDGF BB and IL-1α was about 3 μM. This concentration is readily achievable in vivo in patients with administration of about 300 to 500 mg two or three times daily to a 70 kg person.

We claim:

1. A compound for inhibiting a second messenger pathway, comprising an olefin substituted xanthine core of the formula:

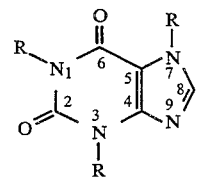

wherein each of one or two R is independently a straight chain hydrocarbon having at least one double bond in a carbon chain length of from about 4 to about 18 carbon atoms in length, wherein multiple double bonds are separated from each other by at least three carbon atoms, wherein the hydrocarbon chain may be substituted by a hydroxyl, halo or dimethylamino group and/or interrupted by an oxygen atom, and wherein the other one or two R is independently H or $CH_3$.

2. The compound of claim 1 wherein each internal double bond is in a cis configuration.

3. The compound of claim 1 wherein the hydrocarbon side chain (R) is bonded to a ring nitrogen of xanthine directly, or through an amino or ether linkage.

4. The compound of claim 1 wherein the length of the hydrocarbon side chain (R) is from six to twelve carbon atoms in length and contains one or two double bonds.

5. The compound of claim 4 which is N-(6-cis-nonenyl)-theobromine.

6. The compound of claim 1 which is N-(2-propenyl)-theobromine.

7. The compound of claim 4 which is N-(6-heptenyl)-theobromine.

8. The compound of claim 4 which is N-(7-octenyl)-theobromine.

9. The compound of claim 4 which is N-(5-hexenyl)-theobromine.

10. The compound of claim 4 which is N-(8-nonenyl)-theobromine.

11. The compound of claim 4 which is N-(9,10-decenyl)theobromine.

12. A pharmaceutical composition comprising a compound of claim 1 and a pharmaceutically acceptable excipient, wherein the pharmaceutical composition is formulated for oral, parenteral or topical administration to a patient.

* * * * *